United States Patent [19]

McCombs et al.

[11] 4,160,165
[45] Jul. 3, 1979

[54] X-RAY DETECTING SYSTEM HAVING NEGATIVE FEEDBACK FOR GAIN STABILIZATION

[75] Inventors: Allan K. McCombs, Bedford; Jay A. Stein, Framingham, both of Mass.

[73] Assignee: American Science and Engineering, Inc., Cambridge, Mass.

[21] Appl. No.: 860,771

[22] Filed: Dec. 15, 1977

Related U.S. Application Data

[63] Continuation of Ser. No. 745,093, Nov. 26, 1976, abandoned.

[51] Int. Cl.² .............................................. G01J 1/42
[52] U.S. Cl. .................................. 250/354; 250/361 R; 250/369; 250/445 T
[58] Field of Search ............... 250/205, 354, 355, 361, 250/369, 445 T

[56] References Cited

U.S. PATENT DOCUMENTS

| | | | |
|---|---|---|---|
| 2,193,789 | 3/1940 | Braselton | 250/205 |
| 3,171,032 | 2/1965 | Holt | 250/205 |
| 3,198,947 | 8/1965 | Arrison et al. | 250/355 |
| 3,670,202 | 6/1972 | Paine et al. | 250/205 |
| 3,903,417 | 9/1975 | Peter | 250/369 |
| 4,032,784 | 6/1977 | Rich | 250/355 |

*Primary Examiner*—Harold A. Dixon
*Attorney, Agent, or Firm*—Pollock, Vande Sande and Priddy

[57] ABSTRACT

An X-ray detecting system includes a number of X-ray detectors mounted on the periphery of a vertical ring rotatable about a patient to be scanned diametrically opposite from an X-ray tube, slit collimator and chopper wheel mounted on the ring. Each detector includes a scintillator crystal typically of NaI, a photomultiplier tube that receives light from the crystal proportional to the incident X-rays, an amplifier energized by the output of the photomultiplier tube that provides a proportional signal to an LED that energizes both the photomultiplier tube (PMT) to provide light feedback and a photodiode that provides an electrical output signal so that the total current at the PMT anode resulting from X-ray light and LED light is constant. Circuitry is preferably included so that the LED supplies only the chopped part of the X-ray equivalent light signal with practically no d-c component.

15 Claims, 4 Drawing Figures

X-RAY DETECTING SYSTEM HAVING NEGATIVE FEEDBACK FOR GAIN STABILIZATION

This is a continuation of application Ser. No. 745,093, filed Nov. 26, 1976, now abandoned.

BACKGROUND OF THE INVENTION

The present invention relates in general to X-ray detecting and more particularly concerns novel apparatus and techniques for providing photoelectric amplification with high stability to provide an output electrical signal accurately representative of the radiant energy provided by incident X-rays.

Tomography comprises taking a number of X-rays at points angularly displaced about the object being X-rayed, such as a head, and processing the X-ray signals thus derived with a computer to provide an image that is a section through the item being examined. Costly apparatus for X-raying brains are commercially available.

It is an important object of this invention to provide an improved system for detecting radiant energy of a type that does not conform to the law of geometric optics (nonconforming radiant energy), such as X- or gamma rays detectable by scintillation detectors, such as sodium iodide crystals, which convert incident radiation into light energy that may be sensed by photoelectric transducers.

It is another object of the invention to achieve the preceding object with a system that is especially useful for detecting in tomography.

It is another object of the invention to achieve one or more of the preceding objects with great stability.

It is another object of the invention to achieve one or more of the preceding objects with apparatus that is relatively inexpensive to fabricate.

It is still a further object of the invention to achieve one or more of the preceding objects with apparatus that is practical to assemble while being rotatable about an object being scanned in conjunction with a source of nonconforming radiant energy.

SUMMARY OF THE INVENTION

In a system according to the invention, there is a source of nonconforming radiant energy, collimating means for forming the nonconforming radiant energy from the source into a fan beam of nonconforming radiant energy incident upon a sector of contiguous scintillation crystal means, modulating means for intermittently interrupting the radiant energy incident upon each scintillation crystal means, and photoelectric transducing means responsive to the light energy incident upon each scintillation crystal means for providing a signal representative of the nonconforming radiant energy incident upon each crystal. Preferably, the source of nonconforming radiant energy, the collimating means and the chopper means are mounted in radial alignment within a first sector of a rotatable support ring diametrically opposite from the sector of the ring that supports the detecting apparatus including the scintillation crystal means and the photoelectric transducing means.

According to a more specific aspect of the invention there is associated with each scintillation crystal means first photoelectric transducing means, such as a photomultiplier tube for transducing light energy incident from the scintillation crystal means into a corresponding electrical signal and amplifying means for amplifying the transduced signal and delivering it to second photoelectric transducing means, such as a light emitting diode (LED) that produces a light feedback signal for illuminating the first photoelectric transducing means and also for illuminating third photoelectric transducing means, such as a photodiode, that provides an output signal for utilization. According to a preferred form of the invention, there is switching means synchronizing with the chopper comprising the modulating means for energizing the second photoelectric transducing means only during intervals when there is incident X-ray energy upon the scintillation crystal means.

Numerous other features, object and advantages of the invention will become apparent from the following specification when read in connection with the accompanying drawing in which:

DETAILED DESCRIPTION OF PREFERRED EMBODIMENTS

Figure 1:
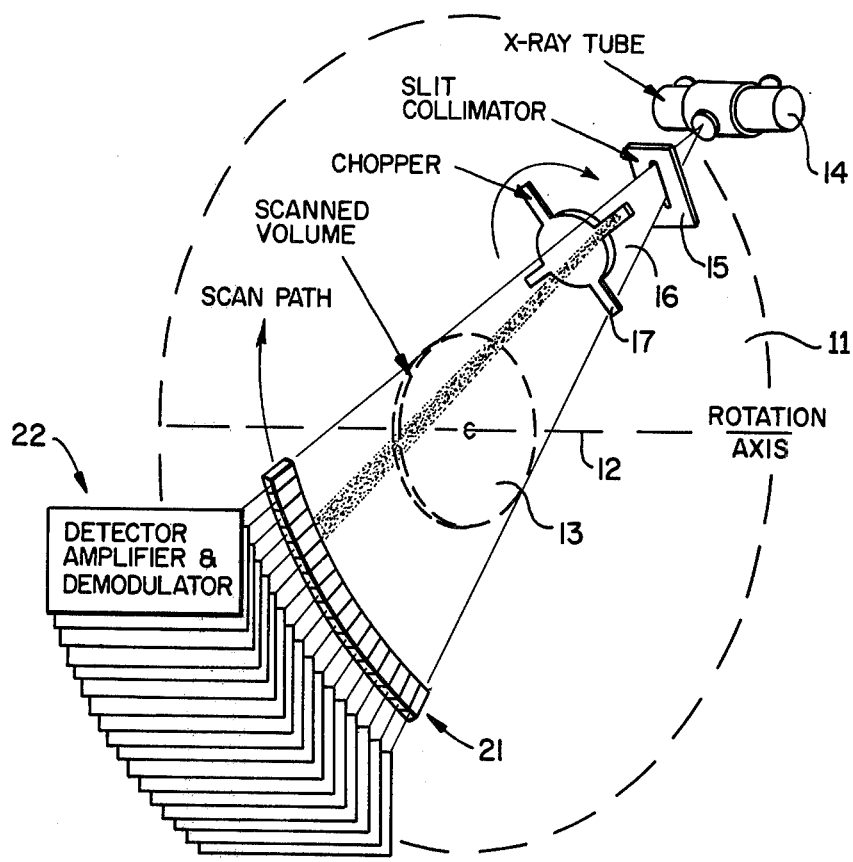
FIG. 1 is a pictorial representation of a rotatable assembly according to the invention.

With reference to FIG. 1, there is shown a pictorial representation of an exemplary embodiment according to the invention. Annular ring 11 rotatable about rotation axis 12 of scanned volume 13 supports in one sector an X-ray tube 14 for providing a beam of X-rays collimated by slit collimator 15 into a fan beam 16 that is modulated by rotating chopper 17. The diametrically opposed portion of ring 11 supports a contiguous array of scintillation detectors 21, typically sodium iodide crystals, that provide light energy to a corresponding group of detector amplifier and demodulators 22 that comprise photoelectric means for converting the incident light energy from the crystals into a corresponding electrical signal representative of the transmissivity through the volume 13 along the chord between a respective one of detectors 21 and X-ray source 14.

In a specific form of the invention there may be 200 detectors 21 mounted on the periphery of ring 11. Ring 11 may be vertical and embrace a horizontal support platform for the patient in the scanned volume 13. The assembly may then rotate about the patient as the horizontal platform translates along the direction of axis 12 to permit one or more sectional X-ray images or a 3-dimensional representation of all or a part of the body of a person or other object being scanned.

Figure 2:
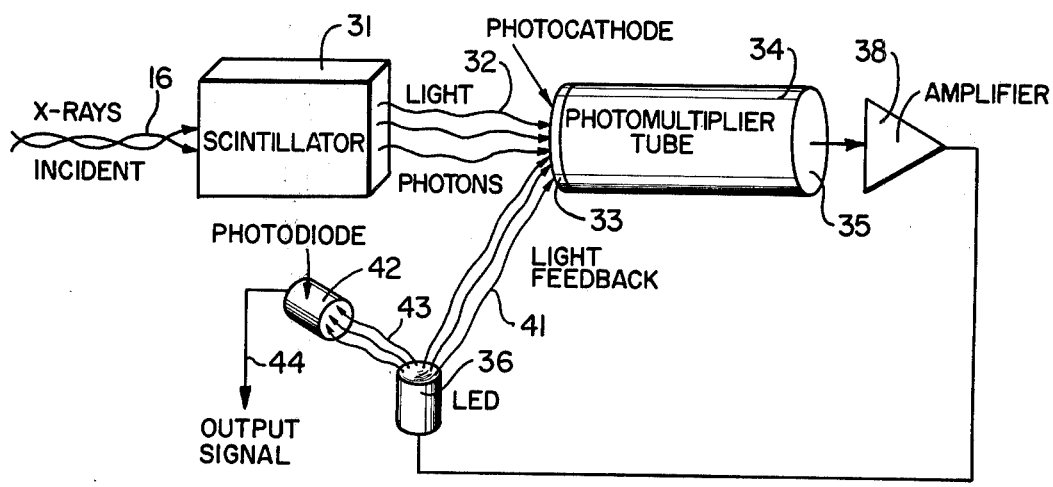
FIG. 2 is a block diagram illustrating the logical arrangement of a system according to the invention.

Referring to FIG. 2, there is shown a block diagram illustrating the logical arrangement of a detecting system according to the invention. Incident X-rays from beam 16 impinge upon scintillator crystal 31 to provide proportional light energy 32 incident upon photocathode 33 of photomultiplier tube 34 that provides an output electrical signal from its anode 35 that is proportional to the light energy incident upon photocathode 33. Amplifier 38 amplifies this signal and delivers it to LED 36 that functions as a photoelectric transducer for converting the incident electrical signal into a corresponding light signal that illuminates photocathode 33 to provide light feedback over path 41 and to illuminate photodiode 42 functioning as a photoelectric transducer for converting the light energy from LED 36 into a corresponding electrical signal on output line 44 in response to the light energy on path 43.

Chopper 17, made of lead or other X-ray opaque material, obscures the primary X-ray flux reaching each scintillation crystal for a short interval of time, typically 20% of a cycle established by controlling the speed of rotation and the number, size and spacing of the spokes while making the chopping frequency large compared to the highest useful frequency in the data signal each detector is to sample. For most practical applications where the highest data frequency of interest is 100 Hz, a chopping frequency of at least 300 Hz is preferred.

During the time interval when a chopper wheel spoke obscures the primary beam, the crystal thus obscured provides a light signal output representative of scattered radiation from parts of the object being scanned irradiated by the remainder of the fan beam. In addition the scintillation crystal may exhibit a property similar to that of the persistence of cathode ray tube phosphors called afterglow. It has been discovered that as much as 5% of the light produced by a NaI crystal from X-ray interaction decays away with time constant much longer (up to seconds) than the main 250 nanosecond decay. For X-ray intensities that vary rapidly in the course of the scan these afterglow components may preclude accurate quantitative measurements since the light emitted by the crystal is a function not only of the current but also the prior X-ray intensity.

A measurement of the detector output signal during the interval when the primary beam is not incident upon the detector is representative of the sum of all scattered radiation and scintillation afterglow. As a result the difference in detector output signal between primary beam-on and primary beam-off conditions is an accurate measurement of the primary transmitted X-ray intensity only and independent of the effects of scattered radiation and scintillation afterglow.

Another advantage of the invention is noise reduction because the difference signal has an error proportional to the noise in the scatter and afterglow signals rather than proportional to the much larger scatter and afterglow signals themselves without compensation.

Still another advantage of the invention is that the output signal is accurately representative of the incident X-ray intensity essentially independent of the gain of the photomultiplier tube. With the arrangement shown in FIG. 2 the light energy provided by LED 36 forces the total current provided by the photomultiplier tube anode tube 35 caused by both scintillation crystal and LED light to be essentially constant. The silicon photodiode 42 measures the amount of light from LED 36 required to maintain this current constant and thereby provides an output signal of peak-to-trough amplitude representative of the X-ray intensity incident upon scintillation crystal 31. Actual measurements of the output of silicon photodiode 42 in an exemplary embodiment with 90 kv on X-ray tube 14 with a beam current of 8 ma resulted in a beam-on signal changing by 25% with the high voltage applied to photomultiplier tube 34 changing from 830 volts to 800 volts whereas the difference between beam-on and beam-off signals (peak-to-trough amplitude) changed by only 0.2 percent. This measured difference signal is independent of the gain of the photomultiplier tube whether caused by high voltage variations, dynode variations or photocathode variations. The difference signal amplitude stability is largely dependent upon the stability of silicon diode 42. For a PIN silicon photodiode, its stability has been found to be better than 0.1% over a relatively wide dynamic range with no observable overload recovery effects, no hysteresis and no drift. The invention thus provides the high light sensitivity of a photomultiplier tube simultaneously with the high stability of a silicon photodiode.

In order to understand the insensitivity of the detecting system according to the invention to changes in photomultiplier tube gain consider the following analysis:

$L_{xon}$ = light intensity due to X-rays during beam-on condition $L_{eon}$ = light intensity due to LED during beam-on condition $L_{xoff}$ = light intensity due to X-rays during beam-off condition $L_{eoff}$ = light intensity due to LED during beam-off condition $g$ = PMT gain—conversion factor from light to anode current The feedback arrangement shown in FIG. 2 forces the total anode current in the PMT in both beam-on and beam-off conditions to be an absolute constant. Therefore:

$$g(L_{xon}+L_{eon}) = \text{constant}$$

$$g(L_{xoff}+L_{eoff}) = \text{constant}$$

or $$L_{xon}-L_{xoff}=L_{eoff}-L_{eon}$$

This shows that the difference in light intensity of the LED between beam-on and beam-off conditions equals the difference in X-ray-produced light between beam-on and beam-off conditions independent of g. (Actually taking into account different spectral content for LED light and X-ray produced light would show these quantities to be proportional rather than equal.) Since the light from the LED detected by the silicon photodiode is directly proportional to the LED light seen by the PMT, the silicon photodiode difference signal is directly proportional to the difference in NaI light between beam-on and beam-off conditions independent of the PMT gain characteristics.

Figure 3:
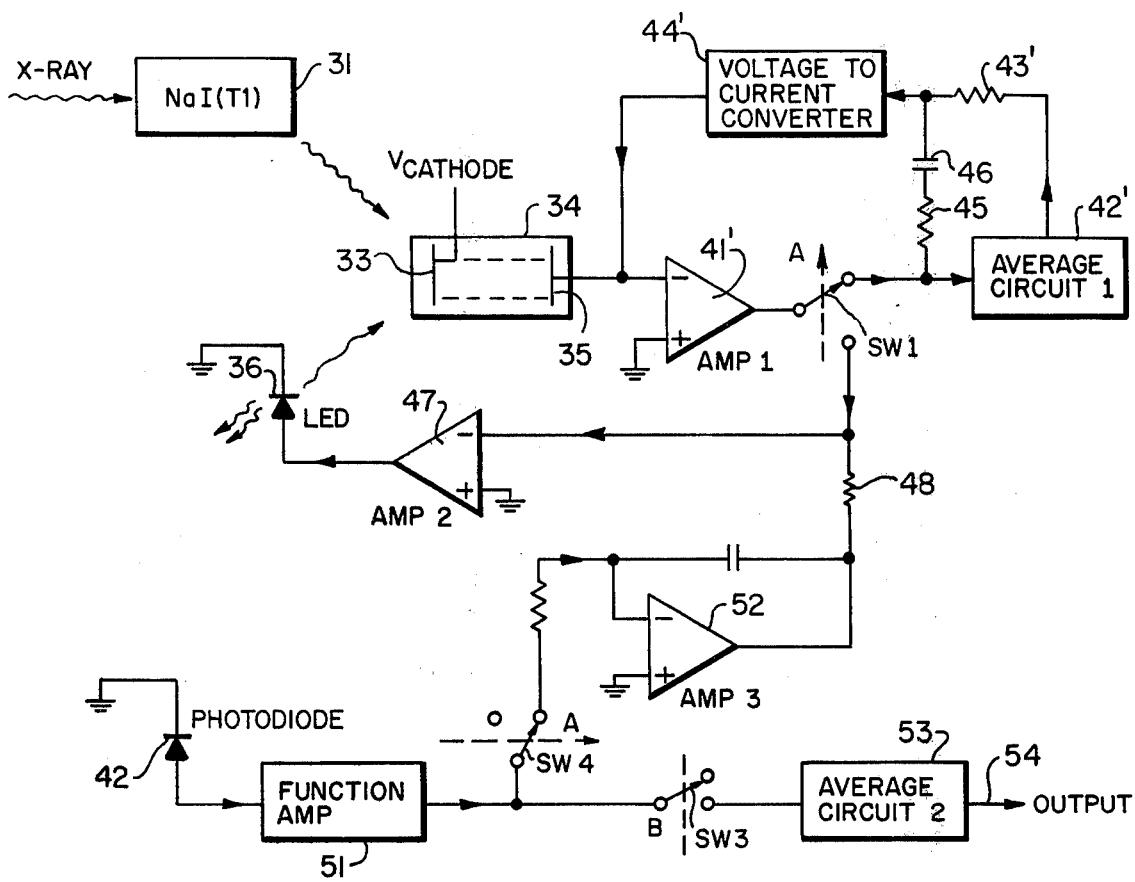
FIG. 3 is a combined block-schematic circuit diagram of a preferred embodiment of the invention with the second photoelectric transducing means providing a signal related only to the chopped part of the X-ray equivalent light signal with practically no D.C. component.

Referring to FIG. 3, there is shown a combined block-schematic circuit diagram of a preferred arrangement of the invention which constrains LED 36 to supply only the chopped part of the X-ray equivalent light signal with practically no D.C. component. Corresponding elements are identified by the same reference symbol throughout the drawing. The means for amplifying comprises a number of differential amplifiers switched in synchronism with the chopper.

The signal on anode 35 is coupled to the −input of a first differential amplifier 41' whose +input is grounded and output connected to the arm of switch SW1 connected as shown in the beam-on condition to the input of a first averaging circuit 42'. Averaging circuit 42' provides an output signal through resistor 43' to the input of voltage-to-current converter 44' with resistor 45 and capacitor 46 functioning to prevent the feedback loop from oscillating. The output of voltage-to-current converter 44' is fed back to the −input of amplifier 41' so that the current out of the voltage-to-current converter 44' is equal to the anode current of the PMT.

In the beam-off condition the arm of switch SW1 couples the output of amplifier 41' to the −input of differential amplifier 47 to energize LED 36 with a signal representative of beam-on condition.

The output of silicon photodiode 42 is coupled to function amplifier 51, preferably having a logarithmic characteristic for accommodating a wide dynamic range. The output of function amplifier 51 is coupled through switch SW4 when the beam is on to the −input of differential amplifier 52 whose +input is grounded to provide an output signal through resistor 48 to the −input of amplifier 47 for providing a fixed baseline in the photodiode 42 current. In the beam-off condition switch SW4 opens and switch SW3 closes so that the output of function amplifier 51 at that time is delivered to the second average circuit 53 and then on output line 54 for further processing.

Figure 4:
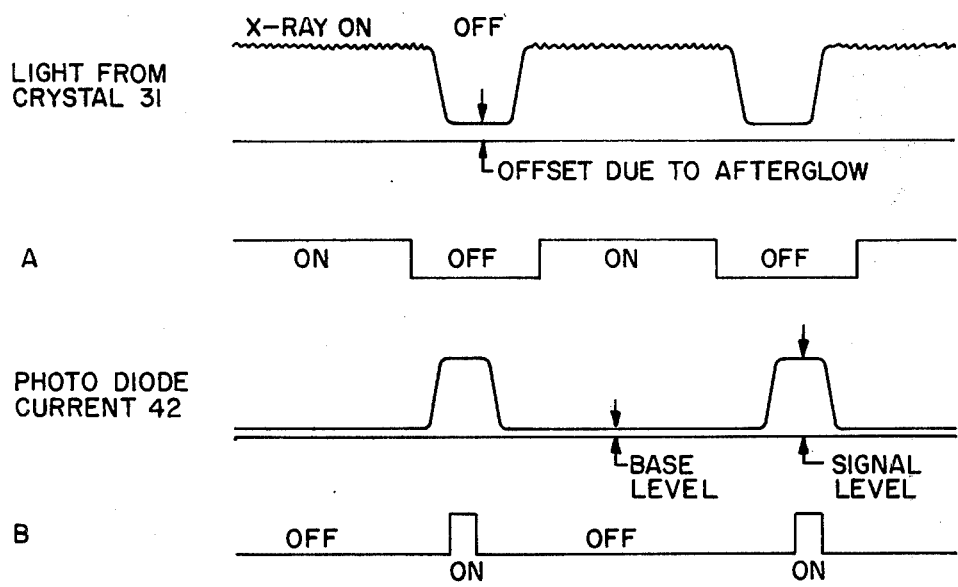
FIG. 4 is a graphical representation of signal waveforms plotted to a common time scale helpful in understanding the principles of operation of the circuit of FIG. 3.

Referring to FIG. 4, there is shown a graphical representation of signal waveforms to a common time scale helpful in understanding the operation of the system of FIG. 3. The second and fourth waveforms designate on and off conditions for the A switches SW1 and SW4 and for the B switch SW3. The first and third waveforms are the light from crystal 31 and the photodiode 42 current, respectively. When the A switches are on, the first averaging circuit 42' averages the photomultiplier tube signal. Simultaneously, the current through diode 50 is held constant by the feedback loop through LED 36. When switch SW4 is open and switch SW1 connects the output of amplifier 41' to the input of amplifier 47, the signal provided by amplifier 41' to amplifier 47 forces LED 36 to increase enough so that the photomultiplier tube anode 35 current remains at the beam-on level. This increase in LED 36 light level is sensed by photodiode 42, amplified and shaped by function amplifier 51, and filtered by the second average circuit 53, to provide an electrical signal 54 representative of the light emitted by the scintillation crystal 31.

There has been described novel apparatus and techniques for detecting nonconforming radiation accurately over a relatively wide dynamic range with reliable equipment requiring negligible calibration and suitable for mounting on a rotatable ring for use in X-ray tomography. It is apparent that those skilled in the art may now make numerous uses and modifications of and departures from the specific embodiments described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. Apparatus for detecting nonconforming radiant energy comprising,
   a source of nonconforming radiant energy,
   scintillation means responsive to said radiant energy for converting said radiant energy for providing a light signal representative of the intensity of said radiant energy incident upon said scintillation means,
   first photoelectric transducing means having an input surface responsive to incident light energy for converting incident light energy on said input surface into a corresponding electrical signal,
   second photoelectric transducing means responsive to an electrical signal for providing an output light signal representative of the input electrical signal,
   means for illuminating said first photoelectric transducing means input surface with light energy from said scintillation means and from said second photoelectric transducing means so that said first photoelectric transducing means provides an electrical output signal representative of the incident combined light signal provided by said scintillation means and said photoelectric transducing means,
   means for coupling the output signal from said first photoelectric transducing means to the input of said second photoelectric transducing means whereby a reduction in the intensity of nonconforming radiant energy is accompanied by an increase in the light energy provided by said second photoelectric transducing means to said first photoelectric transducing means,
   third photoelectric transducing means for converting incident light energy into a representative electrical signal,
   and means for coupling light energy from said second photoelectric transducing means to said third photoelectric transducing means to provide an output signal from said third photoelectric transducing means representative of the nonconforming radiant energy incident upon said scintillation means.

2. Apparatus for detecting nonconforming radiant energy in accordance with claim 1 and further comprising,
   modulating means for periodically interrupting the incidence of nonconforming radiant energy upon said scintillation means.

3. Apparatus for detecting nonconforming radiant energy in accordance with claim 2 wherein said modulating means comprises a chopper wheel of material opaque to said radiant energy positioned between said source of nonconforming radiant energy and said scintillating means.

4. Apparatus for detecting nonconforming radiant energy in accordance with claim 1 and further comprising,
   modulating means for periodically interrupting the incidence of nonconforming radiant energy upon said scintillation means.

5. Apparatus for detecting nonconforming radiant energy in accordance with claim 1 wherein said modulating means comprises a chopper wheel of material opaque to said radiant energy positioned between said source of nonconforming radiant energy and said scintillating means.

6. Apparatus for detecting nonconforming radiant energy in accordance with claim 1 and further comprising,
   an X-ray source comprising the source of said nonconforming radiant energy,
   and collimating means for forming a beam of X-rays emanating from said source upon said scintillation means.

7. Apparatus for detecting nonconforming radiant energy in accordance with claim 6 and further comprising,
means for supporting said collimating means and said X-ray source at a first location and said scintillation means and said photoelectric transducing means at a second location spaced from said first location in fixed relationship thereto.

8. Apparatus for detecting nonconforming radiant energy in accordance with claim 7 wherein said means for supporting comprises a rotatable ring for rotation about an axis in a region to be scanned.

9. Apparatus for detecting nonconforming radiant energy in accordance with claim 7 and further comprising,
modulating means at said first location for periodically interrupting said beam formed by said collimating means.

10. Apparatus for detecting nonconforming radiant energy in accordance with claim 9 wherein said modulating means comprises a chopper wheel of material opaque to said radiant energy positioned between said source of nonconforming radiant energy and said scintillating means.

11. The apparatus of claim 1 wherein said first photoelectric transducing means comprises a photomultiplier tube, said input surface comprising a photocathode in said photomultiplier tube, said second photoelectric transducing means comprising a light-emitting diode, and said third photoelectric transducing means comprising a photodiode.

12. Apparatus for detecting radiant energy comprising,
a first light source for providing an input light signal,
first photoelectric transducing means having an input surface responsive to incident light energy for converting incident light energy on said input surface into a corresponding output electrical signal,
a second light source separate from said first light source, said second light source comprising second photoelectric transducing means responsive to an electrical signal for providing an output light signal representative of the electrical signal,
means for illuminating said first photoelectric transducing means input surface with said input and output light signals so that the latter provides an electrical output signal representative of the combination of said input and output light signals,
means for coupling the output electrical signal from said first photoelectric transducing means to the input of said second light source whereby a reduction and increase in the intensity of said input light signal from said first light source is accompanied by an increase and reduction respectively in the intensity of said output light signal from said second light source,
third photoelectric transducing means for converting incident light energy into a representative electrical signal,
and means for coupling said output light signal to said third photoelectric transducing means to provide an electrical output signal from the latter representative of the intensity of said input light signal.

13. Apparatus for detecting X-ray radiation comprising,
a scintillating crystal responsive to incident X-ray radiation for emitting light to provide an input light signal,
a photomultiplier tube having a photocathode responsive to incident light energy for converting incident light energy on said photocathode into a corresponding output electrical signal,
a light-emitting diode responsive to an electrical signal for providing an output light signal representative of the electrical signal,
means for exposing said photocathode of said photomultiplier tube to the light emitted by said scintillating crystal and to the light emitted by said light emitting diode so that said photomultiplier tube provides an electrical output signal representative of a combination of said input and output light signals,
and means for coupling said output electrical signal from said photomultiplier tube to said light emitting diode whereby a reduction and increase in the intensity of said input light signal from said scintillating crystal is accompanied by an increase and reduction respectively in the intensity of said output light signal from said light emitting diode.

14. The apparatus of claim 13 including a photodiode exposed to light emitted by said light-emitting diode for producing an electrical output signal representative of the X-ray radiation incident on said scintillating crystal.

15. Apparatus for detecting X-rays comprising,
an X-ray source,
a first light source comprising scintillation means responsive to X-rays emitted by said X-ray source for emitting light energy at a level representative of the intensity of the X-ray radiation incident upon said scintillation means,
first photoelectric transducing means having an input surface responsive to incident light energy for converting incident light energy on said input surface into an electrical signal,
a second light source separate from said scintillation means, said second light source comprising second photoelectric transducing means responsive to said electrical signal from said first photoelectric transducing means for emitting light energy at a level related to the magnitude of said electrical signal,
said scintillation means and said first and second transducing means being so positioned relative to one another that said input surface of said first photoelectric transducing means is illuminated by light energy emitted from both said scintillation means and from said second photoelectric transducing means whereby the electrical signal from said first transducing means is representative of the incident combined light energies emitted by said scintillating means and by said second light source, a reduction in the intensity of the X-ray radiation incident on said scintillation means being operative to increase the light energy emitted by said second light source onto said input surface of said first photoelectric transducing means,
and further light-sensitive means responsive to the light energy which is emitted by said second light source for producing an output electrical signal representative of the X-rays incident on said scintillation means.

* * * * *